United States Patent [19]

Sawayama et al.

[11] 4,248,883

[45] Feb. 3, 1981

[54] 1-(3-MERCAPTO-2-METHYLPROPANOYL)-PROLYL AMINO ACID DERIVATIVES AND SALTS THEREOF, PROCESSES FOR THEIR PREPARATION, AND PHARMACEUTICAL COMPOSITIONS CONTAINING SUCH COMPOUNDS

[75] Inventors: Tadahiro Sawayama, Toyonaka; Hiroaki Kinugasa, Yawata; Haruki Nishimura, Ikeda; Kunihiko Takeyama, Ikoma; Kanoo Hosoki, Toyonaka, all of Japan

[73] Assignee: Dainippon Pharmaceutical Co., Ltd., Osaka, Japan

[21] Appl. No.: 53,206

[22] Filed: Jun. 29, 1979

[30] Foreign Application Priority Data

Jul. 6, 1978 [JP] Japan ................................. 53-82809

[51] Int. Cl.³ .................... A61K 31/40; C07D 207/09
[52] U.S. Cl. ............................ 424/274; 260/326.12 R; 260/326.2; 260/326.25; 260/326.42; 260/326.43; 424/273 R; 548/336
[58] Field of Search ............. 260/326.42, 326.2, 326.4, 260/326.47, 326.43; 424/274

[56] References Cited

U.S. PATENT DOCUMENTS

| | | | |
|---|---|---|---|
| 4,046,889 | 9/1977 | Ondetti et al. | 260/326.2 |
| 4,105,776 | 8/1978 | Ondetti et al. | 424/274 |
| 4,116,962 | 9/1978 | Ondetti et al. | 260/326.42 |

OTHER PUBLICATIONS

M. Ondetti, Angiotensin–Science, 196, 441–444, (1977), Design of Specific Angiotension–Converting Enzyme: New Class of Orally Active Antihypertensive Agents.
D. Cushman et al., *Biochemistry*, vol. 16, No. 25, (1977), Design of Potent Competitive Inhibitors of Angiotensin–Converting Enzyme.

*Primary Examiner*—Donald G. Daus
*Assistant Examiner*—M. C. Eakin
*Attorney, Agent, or Firm*—Wenderoth, Lind & Ponack

[57] ABSTRACT

1-(3-Mercapto-2-methylpropanoyl)prolyl amino acid derivatives of the formula

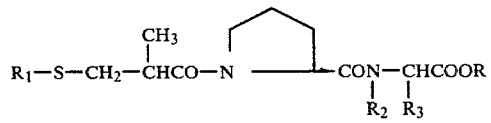

wherein R represents a hydrogen atom, a lower alkyl group, a phenyl-lower alkyl group or a substituted phenyl-lower alkyl group, $R_1$ represents a hydrogen atom, $R_4CO-$, $R_5S-$, or

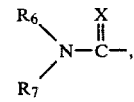

$R_2$ represents a hydrogen atom or a lower alkyl group, $R_3$ represents a hydrogen atom, a phenyl group, a lower alkyl group, or a substituted lower alkyl group, or $R_2$ and $R_3$ form a heterocyclic ring together with the nitrogen and carbon atoms to which they are respectively bonded; salts of these compounds; compositions comprising these compounds or salts; and processes for preparing these compounds or salts. These compounds and salts have excellent antihypertensive activity.

40 Claims, 2 Drawing Figures

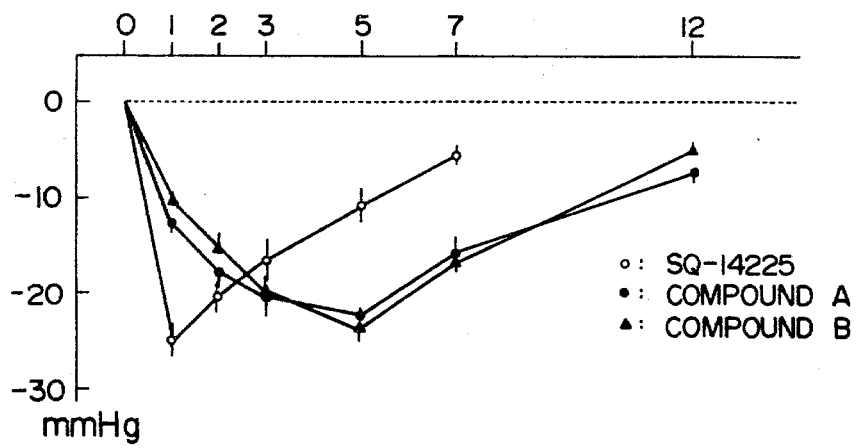
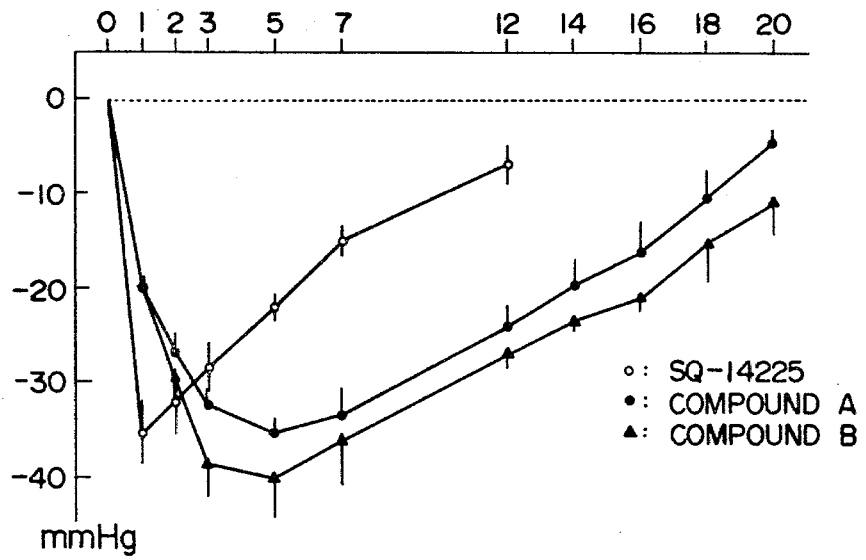

1-(3-MERCAPTO-2-METHYLPROPANOYL)PROLYL AMINO ACID DERIVATIVES AND SALTS THEREOF, PROCESSES FOR THEIR PREPARATION, AND PHARMACEUTICAL COMPOSITIONS CONTAINING SUCH COMPOUNDS

BACKGROUND OF THE INVENTION

This invention relates to novel proline derivatives having antihypertensive activity. More specifically, the invention pertains to 1-(3-mercapto-2-methylpropanoyl)prolyl amino acid derivatives, processes for preparation thereof, and to use of these derivatives as antihypertensive agents.

Recently, Ondetti et al. synthesized various mercaptoalkanoyl amino acids and tested them in vitro for the inhibition of angiotensin I-converting enzyme. Based on this work, they reported that 1-(D-3-mercapto-2-methylpropanoyl)-L-proline (which they termed "SQ-14225") is a particularly good inhibitor of angiotensin I-converting enzyme [Biochemistry, 16, 5484 (1977)]. Ondetti et al. also investigated SQ-14225 and related compounds, and reported that SQ-14225 also has a potent inhibitory activity in vivo on angiotensin I-converting enzyme, and shows superior antihypertensive activity in experimental hypertensive animals based on its inhibitory action [Science 196, 441 (1977)]. U.S. Pat. No. 4,046,889 and DT-OS No. 2,703,828 to Ondetti et al. disclose SQ-14225 and related compounds.

We have made extensive investigations in order to find out pharmacologically better derivatives of SQ-14225 and related compounds, and found that formation of a new peptide bond by introduction of a certain amino acid into the carboxyl group of the proline moiety of SQ-14225 or its derivatives yielded desirable compounds which show a milder onset of antihypertensive activity and a longer duration of such activity than SQ-14225 or its derivatives.

SUMMARY OF THE INVENTION

This invention provides novel 1-(3-mercapto-2-methylpropanoyl)prolyl amino acid derivatives of the formula

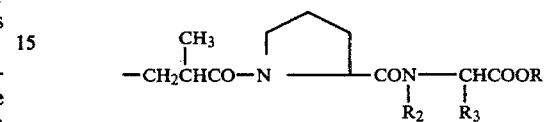

(I)

wherein R represents a hydrogen atom, a lower alkyl group, a phenyl-lower alkyl group or a substituted phenyl-lower alkyl group; $R_1$ represents a hydrogen atom, $R_4CO-$, $R_5S-$ or

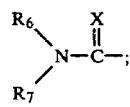

$R_2$ represents a hydrogen atom or a lower alkyl group; $R_3$ represents a hydrogen atom, a phenyl group, a lower alkyl group, or a substituted lower alkyl group in which the substituent is hydroxy, phenyl-lower alkoxy, amino, guanidino, N-nitroguanidino, carboxyl, lower alkoxycarbonyl, phenyl-lower alkoxycarbonyl, carbamoyl, mercapto, lower alkylthio, phenyl, hydroxyphenyl, indolyl or imidazolyl; or $R_2$ and $R_3$ form a heterocyclic ring together with the nitrogen and carbon atoms to which they are respectively bonded; $R_4$ represents a lower alkyl group, a lower alkoxy group, a phenyl group, a substituted phenyl group, a phenyl-lower alkyl group, a substituted phenyl-lower alkyl group, a phenyl-lower alkoxy group, a substituted phenyl-lower alkoxy group, a phenoxy group, or a substituted phenoxy group; $R_5$ represents a lower alkyl group, a phenyl group, a substituted phenyl group, a phenyl-lower alkyl group, a substituted phenyl-lower alkyl group,

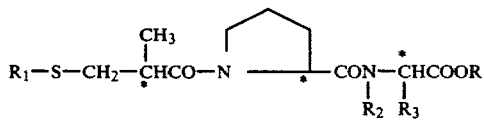

or an amino(-carboxy)lower alkyl group; $R_6$ represents a hydrogen atom or a lower alkyl group; $R_7$ represents a lower alkyl group, a phenyl group or a substituted phenyl group; X represents an oxygen or sulfur atom; and the substituent in the substituted phenyl group is a halogen atom, a lower alkyl group, or a lower alkoxy group; and salts of said derivatives.

The compounds of formula (I) and pharmaceutically acceptable salts thereof have excellent antihypertensive activity based primarily on their ability to inhibit angiotensin I-converting enzyme. This antihypertensive activity is characterized by mild onset and long duration. Accordingly, the compounds of this invention would be very useful in clinical application as antihypertensive agents with a stable efficacy. Because of their characteristic activity, these compounds are expected to remove clinical troubles ascribable to acute hypotension caused by the rapid onset of the action and to reduce inconveniences ascribable to frequent dosing necessitated because of the short duration of the action.

DETAILED DESCRIPTION OF THE INVENTION

The compounds of formula (I) contain at least two asymmetric carbon atoms. The carbon atom at the 2-position of the 3-mercapto-2-methylpropanoyl group, the carbon atom at the 2-position of the proline moiety, and the carbon atom to which $R_3$ is bonded when $R_3$ is other than a hydrogen atom are asymmetric. These carbon atoms are asterisked in formula (I) given above. Accordingly, the compounds of this invention exist as stereoisomers or mixtures thereof. It should be understood that these stereoisomers and mixtures thereof come within the compounds of this invention represented by general formula (I).

The "lower alkyl group" denotes a linear or branched alkyl group containing 1 to 6 carbon atoms, and includes, for example, methyl, ethyl, propyl, isopropyl, butyl, isobutyl, sec-butyl, tert-butyl, pentyl, isopentyl, and hexyl. The lower alkyl group represented by $R_3$ and $R_5$ preferably has 1 to 4 carbon atoms. The lower alkyl group represented by $R_4$ preferably has 1 to 6 carbon atoms. The lower alkyl group represented by R, $R_2$, $R_6$ and $R_7$ preferably has 1 to 4 carbon atoms, especially 1 or 2 carbon atoms. The lower alkyl group represented by $R_3$ can be substituted with the substituent groups indicated hereinabove. The number of such substituents is 1 or 2, preferably only one.

The "lower alkoxy group" denotes a linear or branched alkoxy group containing 1 to 6 carbon atoms, preferably 1 to 4 carbon atoms, especially 1 or 2 carbon atoms. Examples are methoxy, ethoxy, propoxy, isopropoxy, butoxy, isobutoxy, sec-butoxy, and tert-butoxy.

The "phenyl-lower alkyl group" or "substituted phenyl-lower alkyl group" denotes a linear or branched lower alkyl group containing 1 to 6 carbon atoms which is substituted by phenyl or substituted phenyl, preferably substituted or unsubstituted benzyl and substituted or unsubstituted phenethyl, the benzyl being especially preferred.

The "phenyl-lower alkoxy group" denotes a phenyl-lower alkyloxy group in which the phenyl-lower alkyl moiety has the aforesaid meaning, preferably benzyloxy.

The "halogen" denotes fluorine, chlorine, bromine or iodine, chlorine being especially preferred.

Substituents on the benzene ring in the term "substituted phenyl" may include halogen, lower alkyl groups and lower alkoxy groups. The benzene ring is substituted with 1 to 3, preferably only one, such substituent. Preferably, the benzene ring is substituted at the 4-position.

The "heterocyclic ring" which $R_2$ and $R_3$ in formula (I) may form together with the nitrogen and carbon atoms to which they are bonded is a 4- to 8-membered, preferably 4- to 6-membered, heterocyclic ring, and includes, for example, azetidine, pyrrolidine, thiazolidine and piperidine.

The "amino(-carboxy)lower alkyl" denotes a linear or branched alkyl group having 2 to 6 carbon atoms and substituted with one amino and one carboxy. Preferably, the two substituents are positioned on the same carbon atom, for example on the terminal carbon. Examples are 2-amino-2-carboxyethyl, and 2-amino-2-carboxyl-1,1-dimethylethyl.

The group

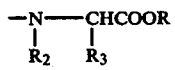

can be derived from an alpha-amino acid. $R_3$ in this grouping is preferably a hydrogen atom, a lower alkyl group or a substituted lower alkyl group in which the substituent is lower alkylthio, phenyl, hydroxyphenyl or indolyl. The lower alkyl group and the substituted lower alkyl group are more preferred. Of these, 2-methylthioethyl, benzyl, p-hydroxybenzyl and 3-indolylmethyl, above all benzyl, are especially preferred. $R_2$ is preferably a hydrogen atom.

Specific examples of the alpha-amino acid include glycine, alanine, valine, leucine, isoleucine, sarcosine, serine, threonine, ornithine, lysine, arginine, aspartic acid, glutamic acid, asparagine, glutamine, cysteine, methionine, phenylalanine, tyrosine, tryptophan, histidine, and proline. Preferred among these are phenylalanine, tyrosine, tryptophan, methionine, alanine, leucine and sarcosine, especially the first four, above all phenylalanine.

R in the above group is preferably a hydrogen atom or a lower alkyl group, especially methyl or ethyl.

$R_1$ in formula (I) is preferably a hydrogen atom, a lower alkanoyl group, a benzoyl group, a lower alkylthio group, a lower alkoxycarbonyl group, a lower alkylcarbamoyl group, a lower alkylthiocarbamoyl group, a di-loweralkyl carbamoyl group, a di-lower alkylthiocarbamoyl group, a phenylcarbamoyl group, a phenylthiocarbamoyl group, or the group

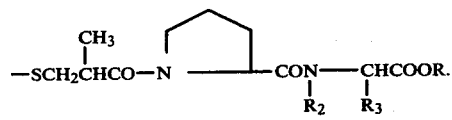

Alkanoyl groups containing 2 to 7 carbon atoms, a benzoyl group and alkylthio groups containing 1 to 4 carbon atoms are especially preferred.

A preferred group of compounds of formula (I) includes those wherein R is a hydrogen atom or a lower alkyl group, $R_1$ is a hydrogen atom, a lower alkanoyl group, a benzoyl group, a lower alkylthio group, a lower alkoxycarbonyl group, a lower alkylcarbamoyl group, a lower alkylthiocarbamoyl group, a di-lower alkylcarbamoyl group, a di-lower alkylthiocarbamoyl group, a phenylcarbamoyl group, a phenylthiocarbamoyl group or the group

$R_2$ is a hydrogen atom or a lower alkyl group; and $R_3$ is a hydrogen atom, a lower alkyl group or a substituted lower alkyl group in which the substituent is lower alkylthio, phenyl, hydroxyphenyl or indolyl. A more preferred group of compounds of formula (I) includes those wherein R and $R_1$ are as stated above; $R_2$ is a hydrogen atom; and $R_3$ is a lower alkyl group, or a substituted lower alkyl group in which the substituent is lower alkylthio, phenyl, hydroxyphenyl or indolyl. A further preferred group of compounds of formula (I) includes those wherein R and $R_1$ are the same as stated above, $R_2$ is a hydrogen atom, and $R_3$ is a 2-methylthioethyl, benzyl, p-hydroxybenzyl or 3-indolylmethyl group.

An especially preferred group of compounds of formula (I) includes those wherein R is a hydrogen atom or an alkyl group containing 1 or 2 carbon atoms, $R_1$ is an alkanoyl group containing 2 to 7 carbon atoms, a benzoyl group or an alkylthio group containing 1 to 4 carbon atoms, $R_2$ is a hydrogen atom, and $R_3$ is a 2-methylthioethyl, benzyl, p-hydroxybenzyl or 3-indolylmethyl group.

The most preferred group of compounds of formula (I) includes those wherein R is a hydrogen atom or an alkyl group containing 1 or 2 carbon atoms, $R_1$ is an alkanoyl group containing 2 to 7 carbon atoms, a benzoyl group or an alkylthio group containing 1 to 4 carbon atoms, $R_2$ is a hydrogen atom, and $R_3$ is a benzyl group.

As stated hereinabove, the compounds of formula (I) have three asymmetric carbon atoms, i.e. the carbon atom at the 2-position of the 3-mercapto-2-methylpropanoyl group, the carbon atom at the 2-position of the proline moiety and the carbon atom to which $R_3$ is bonded when $R_3$ is other than hydrogen. The configurations of the compounds at these asymmetric carbon atoms may be either in the D-form, L-form and DL-form. Generally, the configurations of the proline moiety and $R_3$ are preferably in the L-form, and the configuration of the methyl group at the 2-position of the 3-mercapto-2-methylpropanoyl group is preferably in the D-form.

Examples of suitable compounds of formula (I) are listed below. The first six compounds, especially the first two, are preferred.

1-(D-3-acetylthio-2-methylpropanoyl)-L-prolyl-L-phenylalanine,
1-(D-3-propanoylthio-2-methylpropanoyl)-L-prolyl-L-phenylalanine,
1-[D-3-(2,2-dimethylpropanoyl)thio-2-methylpropanoyl]-L-prolyl-L-phenylalanine,
1-[D-3-(2-methylpropanoyl)thio-2-methylpropanoyl]-L-prolyl-L-phenylalanine,
1-(D-3-ethyldithio-2-methylpropanoyl)-L-prolyl-L-phenylalanine,
1-(D-3-benzoylthio-2-methylpropanoyl)-L-prolyl-L-phenylalanine,
1-(D-3-acetylthio-2-methylpropanoyl)-L-prolyl-L-tyrosine methyl ester,
1-(D-3-acetylthio-2-methylpropanoyl)-L-prolyl-L-tyrosine ethyl ester,
1-(D-3-acetylthio-2-methylpropanoyl)-L-prolyl-L-tryptophan ethyl ester, and
1-(D-3-acetylthio-2-methylpropanoyl)-L-prolyl-L-methionine ethyl ester.

Other examples of compounds of formula (I) are as follows:

1-(D-3-acetylthio-2-methylpropanoyl)-L-prolyl-L-phenylalanine ethyl ester,
1-(D-3-ethoxycarbonylthio-2-methylpropanoyl)-L-prolyl-L-phenylalanine,
1-[D-(3-p-chlorobenzoyl)thio-2-methylpropanoyl]-L-prolyl-L-phenylalanine,
1-(D-3-phenylacetylthio-2-methylpropanoyl)-L-prolyl-L-phenylalanine,
1-[D-3-(p-methoxyphenylacetyl)thio-2-methylpropanoyl]-L-prolyl-L-phenylalanine,
1-(D-3-benzyloxycarbonylthio-2-methylpropanoyl)-L-prolyl-L-phenylalanine,
1-[D-3-(p-methylbenzyloxycarbonyl)thio-2-methylpropanoyl]-L-prolyl-L-phenylalanine,
1-(D-3-phenoxycarbonylthio-2-methylpropanoyl)-L-prolyl-L-phenylalanine,
1-(D-3-phenyldithio-2-methylpropanoyl)-L-prolyl-L-phenylalanine,
1-(D-3-benzyldithio-2-methylpropanoyl)-L-prolyl-L-phenylalanine,
1-(D-3-ethylcarbamoylthio-2-methylpropanoyl)-L-prolyl-L-phenylalanine,
1-(D-3-ethylthiocarbamoylthio-2-methylpropanoyl)-L-prolyl-L-phenylalanine,
1-(D-3-phenylcarbamoylthio-2-methylpropanoyl)-L-prolyl-L-phenylalanine,
1-[D-3-(p-tolylcarbamoyl)thio-2-methylpropanoyl]-L-prolyl-L-phenylalanine,
1,1'-[3,3'-dithiobis(D-2-methylpropanoyl)]-bis(L-prolyl-L-phenylalanine),
1-[D-3-(2-amino-2-carboxyethyl)dithio-2-methylpropanoyl]-L-prolyl-L-phenylalanine,
1-(D-3-acetylthio-2-methylpropanoyl)-L-prolyl-L-phenylalanine benzyl ester,
1-(D-3-propanoylthio-2-methylpropanoyl)-L-prolyl-L-phenylalanine p-methoxybenzyl ester,
1-(D-3-acetylthio-2-methylpropanoyl)-L-prolyl-L-tyrosine,
1-(D-3-acetylthio-2-methylpropanoyl)-L-prolyl-L-tryptophan,
1-(D-3-acetylthio-2-methylpropanoyl)-L-prolyl-L-methionine,
1-(D-3-acetylthio-2-methylpropanoyl)-L-prolyl-L-alanine,
1-[D-3-(2,2-dimethylpropanoyl)thio-2-methylpropanoyl]-L-prolyl-L-leucine,
1-(D-3-propanoylthio-2-methylpropanoyl)-L-prolyl-sarcosine,
1-(D-3-acetylthio-2-methylpropanoyl)-L-prolyl-L-serine,
1-(D-3-propanoylthio-2-methylpropanoyl)-L-prolyl-L-threonine,
1-[D-3-(2-methylpropanoyl)thio-2-methylpropanoyl]-L-prolyl-L-ornithine,
1-(D-3-acetylthio-2-methylpropanoyl)-L-prolyl-L-lysine,
1-(D-3-acetylthio-2-methylpropanoyl)-L-prolyl-L-arginine,
1-(D-3-propanoylthio-2-methylpropanoyl)-L-prolyl-L-aspartic acid,
1-(D-3-acetylthio-2-methylpropanoyl)-L-prolyl-L-glutamic acid,
1-(D-3-acetylthio-2-methylpropanoyl)-L-prolyl-L-asparagine,
1-(D-3-propanoylthio-2-methylpropanoyl)-L-prolyl-L-glutamine,
1-(D-3-acetylthio-2-methylpropanoyl)-L-prolyl-L-cysteine,
1-(D-3-propanoylthio-2-methylpropanoyl)-L-prolyl-L-histidine, and
1-(D-3-acetylthio-2-methylpropanoyl)-L-prolyl-L-(α-phenylglycine).

When in formula (I), R is a hydrogen atom or $R_3$ is amino-lower alkyl, guanidino-lower alkyl or imidazolyl-lower alkyl, the compounds of formula (I) may also be present in the form of salts. The salts of the compounds of formula (I) include salts of compounds of formula (I) in which R is hydrogen with inorganic or organic bases, and acid addition salts of compounds of formula (I) in which $R_3$ is amino-lower alkyl, guanidino-lower alkyl or imidazolyl-lower alkyl with inorganic or organic acids. The salts with inorganic bases include alkali metal salts (e.g., sodium or potassium salts), alkaline earth metal salts (e.g., calcium or magnesium salts), and ammonium salts. The salts with organic bases include salts with dicyclohexylamine, benzathine, hydrabamine, and lysine. The acid addition salts with inorganic acids include hydrochlorides, hydrobromides, sulfates and phosphates. The acid addition salts with organic acids include acetates, tartrates, lactates, maleates and methanesulfonates. Pharmaceutically acceptable salts are especially preferred.

According to this invention, the compounds of formula (I) or salts thereof can be produced by (a) reacting a compound of formula (II)

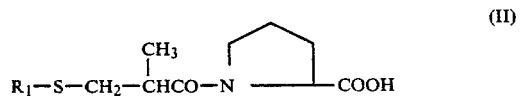

(II)

wherein $R_1$ is as defined hereinabove, or its reactive derivative at its carboxyl group, with a compound of formula (III)

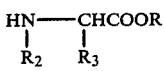

(III)

wherein R, R₂ and R₃ are as defined hereinabove, and a functional group optionally present in R₃ may be protected, or (b) reacting a compound of formula (IV)

(IV)

wherein R₁ is as defined hereinabove, or its reactive derivative at its carboxyl group, with a compound of formula (V)

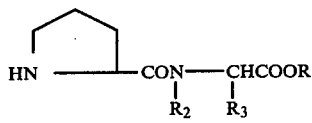

(V)

wherein R, R₂ and R₃ are as defined hereinabove, and a functional group optionally present in R₃ may be protected;
and if desired, splitting off the protective group present in the resulting compound to convert the protected functional group into a free functional group; and if desired, converting the compound of formula (I) to another compound of formula (I); and/or, if desired, converting the compound of formula (I) into its salt; and/or, if desired, when the compound of formula (I) is present as a mixture of stereoisomers, separating it into the individual stereoisomers.

Functional groups present in group R₃ in formulae (III) and (V), i.e. hydroxy, amino, guanidino, carboxyl, mercapto and imidazolyl, may be protected with protective groups normally used in the field of peptide syntheses. Protective groups for hydroxy are, for example, benzyl, tert-butoxycarbonyl, and benzyloxycarbonyl. Protective groups for amino are, for example, benzyloxycarbonyl and tert-butoxycarbonyl. Nitro and tosyl are examples of protective groups for guanidino. Examples of protective groups for carboxyl are benzyl, p-nitrobenzyl, tert-butyl and benzhydryl. Protective groups for mercapto are, for example, benzyl and p-methoxybenzyl. Protective groups for imidazolyl are, for example, benzyloxycarbonyl and tosyl.

The reaction (a) between the compound of formula (II) or its reactive derivative at its carboxyl group and the compound of formula (III), and the reaction (b) between the compound of formula (IV) or its reactive derivative at its carboxyl group and the compound of formula (V) can be performed in accordance with amidation methods known in the field of peptide syntheses. These methods are described in detail, for example, in Methoden der Organischen Chemie (Houben-Weyl), Vol. XV, Parts I and II (1974).

The reaction (a) and the reaction (b) are usually carried out by contacting the two starting compounds in an inert solvent. The inert solvent used should be properly chosen depending upon the types of the starting compounds, etc. Examples are tetrahydrofuran, dioxane, chloroform, dichloromethane, ethyl acetate, acetone, acetonitrile, dimethylformamide, dimethyl sulfoxide, pyridine and water. These solvents are used either singly or as a mixture. If required, these reactions are carried out in the presence of bases. Specific examples of the bases are alkali metal bicarbonates such as sodium bicarbonate and potassium bicarbonate, alkali metal carbonates such as sodium carbonate and potassium carbonate, alkali metal hydroxides such as sodium hydroxide and potassium hydroxide, and organic bases such as triethylamine, tri-n-butylamine, N-methylmorpholine and dicyclohexylamine.

The compound of formula (III) or (V) may be used in the form of an acid addition salt. In this case, the compound of formula (III) or (V) in free form can be obtained by adding an equivalent amount of the aforesaid base to the reaction system.

The reaction temperature varies depending upon the types of the starting compounds, etc., but usually it is within the range of about −50° C. to about 60° C.

The ratio between the compound of formula (III) and the compound of formula (II) or its reactive derivative, and the ratio between the compound of formula (V) and the compound of formula (IV) or its reactive derivative are not critical, and can be varied widely according to the types of the starting materials used. Generally, it is advantageous that about 1 to about 1.5 moles of the compound of formula (III) is used per mole of the compound of formula (II) or its reactive derivative, and about 1 to about 1.5 moles of the compound of formula (IV) or its reactive derivative is used per mole of the compound of formula (V).

When the compound of formula (II) or the compound of formula (IV) is to be reacted as such with the compound of formula (III) or the compound of formula (V), the reaction is advantageously carried out in the presence of a coupling agent such as dicyclohexylcarbodiimide, N,N'-carbonyldiimidazole, Woodward reagent K or 1-ethoxycarbonyl-2-ethoxy-1,2-dihydroquinoline.

Reactive derivatives at the carboxyl group of the compounds of formula (II) or (IV) include any reactive derivatives which are normally used in the field of peptide syntheses. Specific examples include mixed anhydrides formed with acids such as alkylcarbonic acids (e.g., ethylcarbonic acid or isobutylcarbonic acid), arylcarbonic acids (e.g., phenylcarbonic acid), alkylcarboxylic acids (e.g., isovaleric acid or pivalic acid), phosphoric acids (e.g., diethylphosphoric acid), and sulfonic acids (e.g., methanesulfonic acid or p-toluenesulfonic acid); reactive esters such as p-nitrophenyl esters, 2,4,5-trichlorophenyl esters, pentachlorophenyl esters, p-nitrophenylthio esters, cyanomethyl esters, N-hydroxypiperidine esters, N-hydroxysuccinimide esters, and N-hydroxyphthalimide esters; symmetrical anhydrides; acid halides such as acid chlorides; and acid azides. The mixed anhydrides or reactive esters are especially preferred as the reactive derivatives of the compound of formula (II), and the acid halides (especially acid chlorides), mixed anhydrides and reactive esters, as the reactive derivatives of the compound of formula (IV). These reactive derivatives can be synthesized in accordance with conventional methods.

Splitting off of the protective group optionally present in group R₃ of the compounds of formula (I) obtained by the above methods can be performed in a customary manner. For example, the protective groups can be split off by using liquid hydrogen fluoride, trifluoroacetic acid, hydrogen bromide/acetic acid, and hydroxylamine. For details of deprotection, reference may be had to the "Methoden der Organischen Chemie" cited hereinabove.

Compounds of formula (I) in which R is hydrogen can be converted to various corresponding esters by esterification, for example by reacting these compounds or their reactive derivatives at the carboxyl group (e.g., the mixed anhydrides or reactive esters) with compounds of the formula R'OH in which R' is the same as R excepting a hydrogen atom.

Compounds of formula (I) in which R is other than hydrogen can be converted into the corresponding compounds in which R is hydrogen in a customary manner, for example by alkaline hydrolysis or by treatment with trifluoroacetic acid or liquid hydrogen fluoride to split off the group R. Compounds of formula (I) in which R is a tert-butyl group can be easily converted to the corresponding compounds of formula (I) in which R is hydrogen, for example, by treating them with trifluoroacetic acid and anisole.

Compounds of formula (I) in which $R_1$ represents the groups other than hydrogen atom can be converted to the corresponding compounds of formula (I) in which $R_1$ is hydrogen by splitting off the group $R_1$ in a customary manner, for example by ammonolysis, alkaline hydrolysis or treatment with zinc/mineral acid. In particular, compounds of formula (I) in which $R_1$ is lower alkanoyl, phenyl-lower alkanoyl, benzoyl or lower alkylcarbamoyl can be easily converted to compounds of formula (I) in which $R_1$ is a hydrogen atom by ammonolysis (for example, treatment with alcoholic ammonia or concentrated ammonium hydroxide solution), alkaline hydrolysis (for example, treatment with aqueous metal hydroxide), or treatment with hydrazine or hydroxylamine.

Compounds of formula (I) in which $R_1$ is a hydrogen atom can be converted to the corresponding compounds of formula (I) in which $R_1$ represents the defined groups other than hydrogen by the following methods.

(i) Compounds of formula (I) in which $R_1$ is the group $R_4CO-$ can be obtained by reacting compounds of formula (I) in which $R_1$ is hydrogen with compounds of formula (VI)

$$R_4'COOH \qquad (VI)$$

wherein $R_4'$ represents a lower alkyl group, a phenyl group, a substituted phenyl group, a phenyl-lower alkyl group, or a substituted phenyl-lower alkyl group, or the reactive derivatives thereof (e.g., acid halides including acid chlorides and acid bromides, or symmetrical acid anhydrides), or with compounds of formula (VII)

$$R_4'OCOY \qquad (VII)$$

wherein $R_4'$ is as defined above, and Y represents a halogen atom such as chlorine or bromine, in a customary manner.

(ii) Compounds of formula (I) in which $R_1$ is the group $R_5'S-$ in which $R_5'$ represents a lower alkyl group, a phenyl group, a substituted phenyl group, a phenyl-lower alkyl group, a substituted phenyl-loweralkyl group, or an amino(-carboxyl)lower alkyl group can be obtained by reacting compounds of formula (I) in which $R_1$ is a hydrogen atom with compounds of formula (VIII) or (IX)

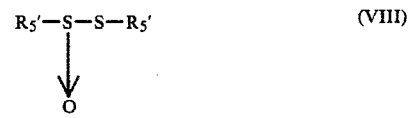

$$R'_5-S-SO_3M \qquad (IX)$$

wherein $R'_5$ is as defined hereinabove, and M is a metal atom in a customary manner.

(iii) Symmetrical disulfides of formula (I) in which $R_1$ is

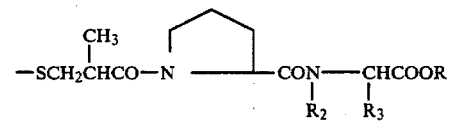

can be obtained by oxidizing compounds of formula (I) in which $R_1$ is a hydrogen atom in a customary manner, for example with iodine.

(iv) Compounds of formula (I) in which $R_1$ is

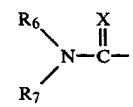

can be obtained by reacting compounds of formula (I) in which $R_1$ is a hydrogen atom with compounds of formula (X) or (XI)

$$R_7-N=C=X \qquad (XI)$$

wherein $R_7$, X and Y are as defined hereinabove, and $R'_6$ is a lower alkyl group, in a customary manner.

When a functional group optionally present in group $R_3$ is likely to react with the reagents in practicing the methods (i) to (iv), the functional group should desirably be protected.

Synthetic methods for the various derivatives of mercapto compounds mentioned above are described in detail, for example, in Methoden der Organischen Chemie (Houben-Weyl), Vol. IX, 1-915 (1955). Experimental details of the methods (i) to (iv) are found in Examples given hereinbelow.

The compounds of formula (I) formed by the aforesaid reactions can be isolated and separated by conventional procedures such as extraction, chromatography and recrystallization.

The starting compound (II), (III), (IV), or (V) in the above-described manufacturing methods may be a racemic mixture or one of the stereoisomers. To obtain the desired stereoisomer, the configurations of the proline moiety and $R_3$ in the starting material (II), (III) or (V) should preferably be made identical with those of the final desired product. In this case, the configuration of the methyl group at the 2-position of the 3-mercapto-2-methylpropanoyl group in the starting compound (I) or (IV) may be in the DL-form. In this case, the stereoisomers obtained in the product may be separated by a conventional chromatographic or fractional crystallization method.

Compounds of formula (I) in which R is a hydrogen atom form salts with various inorganic bases or organic bases, and compound of formula (I) in which $R_3$ is an amino-lower alkyl group, a guanidino-lower alkyl group or an imidazolyl-lower alkyl group form salts with various inorganic or organic acids. Salt formation can be carried out in a customary manner.

More specific processes for producing the compounds of this invention will become apparent from Examples given hereinbelow.

Some of the compounds of formula (II) used as a starting material in the reaction (a) are known. Novel species within formula (II) can be easily produced in accordance with the methods described, for example, in U.S. Pat. No. 4,046,889, DT-OS No. 2,703,828, and Biochemistry 16, 5484 (1977). The compounds of formula (III) as another starting material are available on the market, or can be easily prepared by known methods.

Some of the compounds of formula (IV) used as a starting material in the reaction (b) are known, and novel species within formula (IV) can be produced in accordance with the methods described, for example, in U.S. Pat. No. 4,046,889 and DT-OS No. 2,703,828. The compounds of formula (V), another starting material, can be easily produced from proline and alpha-amino acids in accordance with conventional methods in the synthesis of peptides.

The compounds of the invention expressed by formula (I) and the pharmaceutically acceptable salts thereof have excellent antihypertensive activity based primarily on their ability to inhibit angiotensin I-converting enzyme.

The results of pharmacological tests on some typical compounds of this invention are shown below. The following compounds were used in the experiments.

COMPOUNDS OF THE INVENTION

A: 1-(D-3-Acetylthio-2-methylpropanoyl)-L-prolyl-L-phenylalanine

B: 1-(D-3-Propanoylthio-2-methylpropanoyl)-L-prolyl-L-phenylalanine

C: 1-[D-3-(2,2-Dimethylpropanoyl)thio-2-methylpropanoyl]-L-prolyl-L-phenylalanine D: 1-[D-3-(2-Methylpropanoyl)thio-2-methylpropanoyl]-L-prolyl-L-phenylalanine E: 1-(D-3-Ethyldithio-2-methylpropanoyl)-L-prolyl-L-phenylalanine F: 1-(D-3-Benzoylthio-2-methylpropanoyl)-L-prolyl-L-phenylalanine G: 1-(D-3-Acetylthio-2-methylpropanoyl)-L-prolyl-L-tyrosine methyl ester H: 1-(D-3-Acetylthio-2-methylpropanoyl)-L-prolyl-L-tyrosine ethyl ester I: 1-(D-3-Acetylthio-2-methylpropanoyl)-L-prolyl-L-tryptophan ethyl ester J: 1-(D-3-Acetylthio-2-methylpropanoyl)-L-prolyl-L-methionine ethyl ester

CONTROL COMPOUNDS

1: 1-(D-3-Mercapto-2-methylpropanoyl)-L-proline (SQ-14225)

2: 1-(D-3-Mercapto-2-methylpropanoyl)-L-proline amide disclosed in U.S. Pat. No. 4,046,889

3: 1-(D-3-Acetylthio-2-methylpropanoyl)-L-proline amide which is novel but comes within the general formula given in U.S. Pat. No. 4,046,889.

TEST 1: ANTIHYPERTENSIVE ACTIVITY

Male STD Wistar strain rats, about 8 weeks old and weighing 185 to 195 grams, were anesthetized with ether and a silver clip, 0.20 mm wide, was placed on the left renal artery through a flank incision. The contralateral kidney and its renal artery were left intact. The animals were maintained on commercial rat chow and tap water ad libitum.

These experimental animals are called Goldblatt two-kidney renal hypertensive rats, and are believed to have a typical case of hypertension which depends upon the increased activity of the renin-angiotensin system [Science, 188, 1316 (1975)].

The animals were used 10 to 21 days after the clipping, when the blood pressures approached 180 to 220 mmHg. The test compounds were orally administered to the animals in a dose of 0.1 millimole/kg of body weight. Blood pressures were measured just before and 1, 2, 3, 5, 7, 12, 14, 16, 18, 20, 22 and 24 hours after the administration by the tailplethysmographic method without anesthesia.

The following table summarizes the initial blood pressures of the test animals, the time at which the maximum hypotensive effect was observed (peak time), and the changes in blood pressure both at the peak time and 7 hours after the administration. The extent of hypotensive activity at 7 hours is considered to be a good measure for evaluating the duration of the action of the test compounds.

| Test compound | Initial blood pressure (mmHg) | Peak time (hours) | Change in blood pressure, mmHg (%) | |
|---|---|---|---|---|
| | | | Peak time | 7 hours after administration |
| A | 201 | 5 | −35 (−17) | −33 (−16) |
| B | 217 | 5 | −40 (−18) | −36 (−17) |
| C | 204 | 5 | −41 (−20) | −37 (−18) |
| D | 204 | 5 | −37 (−18) | −29 (−14) |
| E | 202 | 7 | −38 (−19) | −38 (−19) |
| F | 213 | 5 | −31 (−15) | −31 (−15) |
| G | 198 | 5 | −33 (−17) | −29 (−15) |
| H | 201 | 5 | −34 (−17) | −29 (−14) |
| I | 183 | 5 | −30 (−16) | −26 (−14) |
| J | 206 | 5 | −30 (−15) | −27 (−13) |
| 1 | 195 | 1 | −35 (−18) | −15 (−8) |
| 2 | 196 | 2 | −5 (−3) | −1 (−1) |
| 3 | 197 | 2 | −7 (−4) | −4 (−2) |

The above table demonstrates that compounds A to J produced a maximum hypotensive response (a 15–20% decrease in initial blood pressure) at 5 to 7 hours after medication, while compound 1 (SQ-14225) showed a maximum response (18% decrease) at 1 hour after medication. At 7 hours after the medication, compounds A to J gave considerable hypotensive responses with a decrease of about 13 to 19% in initial blood pressure, but compound 1 (SQ-14225) showed a decrease of only 8% in initial blood pressure. These data suggest that the hypotensive potencies of compounds A to J are comparable to that of compound 1 (SQ-14225) and the onset of the hypotensive action of compounds A to J is milder, and the duration of the action of these compounds is much longer, than that of compound 1 (SQ-14225). On the other hand, compound 2 (a simple amide derivative of SQ-14225) and compound 3 (a simple amide derivative of S-acetyl SQ-14225) did not reduce blood pressures.

FIGS. 1 and 2 accompanying the present application show the time courses of changes in blood pressure of the two-kidney renal hypertensive rats after a single oral administration (0.015 millimole/kg and 0.1 millimole/kg) of compounds A and B and compound 1 (SQ-14225). In each Figure, the ordinate represents the changes in blood pressure (mmHg) and the abscissa, the time (hours) elapsed after oral administration. Each point shows a mean value taken from six animals and the vertical lines indicate standard errors.

These graphic representations clearly show that compounds A and B have milder and more prolonged antihypertensive effect than does compound 1 (SQ-14225).

TEST 2: TOXICITY

Male STD-ddY strain mice, weighing 21 to 24 grams, were used. The oral $LD_{50}$ values of compounds A and B in the mice were found to be more than 6 g per kilogram of body weight, and the intravenous $LD_{50}$ values of these compounds, more than 1 g per kilogram of body weight. These data show that the toxicities of compounds A and B are very weak.

The foregoing experimental results demonstrate that the compounds of formula (I) and the pharmaceutically acceptable salts thereof exhibit excellent antihypertensive activity with weak toxicity, and therefore, can be used an antihypertensive drugs in treating hypertension in mammals including humans. These compounds are especially useful for treating hypertension based on the increased activity of the renin-angiotensin system.

The route of administration of the compounds of this invention may be oral, parenteral or intrarectal, but preferably, they are administered orally. The dosage of the compound of formula (I) or the pharmaceutically acceptable salt thereof varies depending upon the type of such an antihypertensive compound, the method of administration, and the condition, age, etc. of the patient. The total daily dose is generally 0.1 to 200 mg per kg of body weight, preferably 0.2 to 50 mg per kg of body weight, in administration to man. The drug is taken once or twice a day in the total doses indicated.

Usually, the compound of formula (I) or its pharmaceutically acceptable salt is administered to a subject in the form of a pharmaceutical composition comprising a therapeutically effective and non-toxic amount of such a compound. The pharmaceutical composition is formulated by mixing the compound of formula (I) or its pharmaceutically acceptable salt with a pharmaceutically acceptable carrier. Suitable carriers are those which are customarily used in formulating pharmaceuticals and do not react with the compounds of formula (I) or the salts thereof. Specific examples of such carriers include lactose, starch, sucrose, microcrystalline cellulose, sodium carboxymethyl cellulose, calcium carboxymethyl cellulose, methylcellulose, gelatin, acacia, hydroxypropylcellulose, hydroxypropyl methylcellulose, polyvinylpyrrolidone, light anhydrous silicic acid, magnesium stearate, talc, titanium dioxide, sorbitan fatty acid esters, glycerides of saturated fatty acids, macrogol, propylene glycol, and water. The pharmaceutical composition may be in various dosage forms such as tablets, capsules, granules, fine granules, powders, syrups, suppositories, and injections which are formulated in a customary manner. Liquid preparations may be in such a form as to be dissolved or suspended in water or other suitable vehicles just prior to use. The tablets may be coated in known manner. If desired, the pharmaceutical composition may contain flavoring agents, aromatics, preservatives, buffers, salts for rendering the composition isotonic, etc.

Usually, the pharmaceutical composition may contain at least 0.5%, preferably 1 to 60%, of the compound of formula (I) or its pharmaceutically acceptable salt as an active ingredient. The composition may also contain other terapeutically effective compounds.

The following Examples and Referential Examples illustrate the present invention more specifically. It should be understood however that the invention is not limited to these Examples. The parenthesized compounds given after the indication of melting points are recrystallizing solvents.

EXAMPLE 1

1-(D-3-Acetylthio-2-methylpropanoyl)-L-prolylglycine ethyl ester

N-Methylmorpholine (0.39 g) was added to a solution of 1-(D-3-acetylthio-2-methylpropanoyl)-L-proline (1.0 g) in dry tetrahydrofuran (20 ml). The resulting solution was stirred and cooled at −20° to −15° C. Phenyl chloroformate (0.61 g) was added, and after 5 minutes, a solution of glycine ethyl ester hydrochloride (0.54 g) and N-methylmorpholine (0.39 g) in dry tetrahydrofuran (20 ml) was added. The mixture was stirred at −20° to −15° C. for one hour and then at room temperature overnight.

After removal of insoluble materials by filtration, the filtrate was concentrated under reduced pressure and the residue was dissolved in dichloromethane. The solution was washed successively with 1 N sodium hydroxide, water, 1 N hydrochloric acid, and water, dried over sodium sulfate, and concentrated under reduced pressure. The residue was chromatographed on silica gel with chloroform to give the title compound (0.8 g).

IR $\nu_{max}^{NaCl}$ cm$^{-1}$: 3270, 1740, 1680, 1630, 1620.

The following compounds were prepared in substantially the same manner as in Example 1:

1-(3-acetylthio-2-methylpropanoyl)-L-prolylglycine ethyl ester;

1-(D-3-acetylthio-2-methylpropanoyl)-L-prolyl-L-alanine ethyl ester, IR $\nu_{max}^{NaCl}$ cm$^{-1}$: 3250, 1725, 1675, 1610;

1-(D-3-acetylthio-2-methylpropanoyl)-L-prolyl-L-proline benzyl ester, IR $\nu_{max}^{NaCl}$ cm$^{-1}$: 1730, 1680, 1650(sh), 1630;

1-(D-3-acetylthio-2-methylpropanoyl)-L-prolyl-L-aspartic acid α,β-dibenzyl ester, IR $\nu_{max}^{NaCl}$ cm$^{-1}$: 3250, 1725, 1685, 1630;

1-(D-3-acetylthio-2-methylpropanoyl)-L-prolyl-L-phenylalanine ethyl ester, m.p. 55°–57° C. (diethyl ether), IR $\nu_{max}^{KBr}$ cm$^{-1}$: 3240, 1730, 1680, 1630;

1-(D-3-acetylthio-2-methylpropanoyl)-L-prolyl-O-benzyl-L-threonine benzyl ester, IR $\nu_{max}^{NaCl}$ cm$^{-1}$: 3270, 1735, 1680, 1620; and 1-(D-3-acetylthio-2-methylpropanoyl)-L-prolyl-L-methionine ethyl ester, IR $\nu_{max}^{NaCl}$ cm$^{-1}$: 1730, 1680, 1620.

EXAMPLE 2

1-(D-3-Acetylthio-2-methylpropanoyl)-L-prolyl-L-tyrosine ethyl ester

The procedure described in the first paragraph of Example 1 was repeated using L-tyrosine ethyl ester hydrochloride (0.95 g) in place of glycine ethyl ester hydrochloride.

After removal of insoluble materials by filtration, the filtrate was concentrated under reduced pressure and the residue was dissolved in chloroform. The solution was washed successively with aqueous sodium bicarbonate, water, 1 N hydrochloric acid, and water, dried over sodium sulfate, and concentrated under reduced pressure. The residue was chromatographed on silica gel with chloroform to give the title compound (1.4 g).

IR $\nu_{max}^{NaCl}$ cm$^{-1}$: 3250, 1725, 1675, 1650(sh), 1605.

EXAMPLE 3

1-(D-3-Acetylthio-2-methylpropanoyl)-L-prolyl-L-tryptophan ethyl ester

The procedure described in the first paragraph of Example 1 was repeated using L-tryptophan ethyl ester hydrochloride (1.03 g) in place of glycine ethyl ester hydrochloride. The chloroform solution obtained as in Example 2 was washed with 1 N sodium hydroxide and then with water, dried over sodium sulfate, and concentrated under reduced pressure. The residue was chromatographed on silica gel with chloroform to give the title compound (1.32 g).

IR $\nu_{max}^{NaCl}$ cm$^{-1}$: 3260, 1730, 1675, 1615.

EXAMPLE 4

1-(D-3-Acetylthio-2-methylpropanoyl)-L-prolyl-L-tyrosine methyl ester

N-Methylmorpholine (0.39 g) was added to a solution of 1-(D-3-acetylthio-2-methylpropanoyl)-L-proline (1.0 g) in dry tetrahydrofuran (20 ml). The resulting solution was stirred and cooled at −20° to −15° C. Phenyl chloroformate (0.61 g) was added, and after 5 minutes, L-tyrosine methyl ester (0.75 g) was added. The mixture was stirred at −20° to −15° C. for one hour and then at room temperature overnight.

The chloroform solution obtained as in Example 2 was washed with 1 N hydrochloric acid and then with water, dried over sodium sulfate, and concentrated under reduced pressure. The residue was chromatographed on silica gel with chloroform-methanol (99:1) to give the title compound (1.15 g) as a clear and viscous oil, which solidified on standing, m.p. 62°–65° C.

IR $\nu_{max}^{KBr}$ cm$^{-1}$: 3250, 1725, 1670, 1650(sh), 1605.

EXAMPLE 5

1-(D-3-acetylthio-2-methylpropanoyl)-L-prolyl-L-tyrosine tert-butyl ester

N-Methylmorpholine (1.17 g) was added to a solution of 1-(D-3-acetylthio-2-methylpropanoyl)-L-proline (3.0 g) in dry tetrahydrofuran (60 ml). The resulting solution was stirred and cooled at −20° to −15° C. Phenyl chloroformate (1.82 g) was added, and after 5 minutes, L-tyrosine tert-butyl ester (2.63 g) was added. The mixture was stirred at −20° to −15° C. for one hour and then at room temperature overnight. The chloroform solution obtained as in Example 2 was washed successively with 4% sodium bicarbonate, water, 10% citric acid, and water, dried over sodium sulfate, and concentrated under reduced pressure. The residue was chromatographed on silica gel with chloroform-methanol (99:1) to give the title compound (4.2 g) as a viscous oil.

IR $\nu_{max}^{NaCl}$ cm$^{-1}$: 3250, 1715, 1670, 1610.

EXAMPLE 6

1-(D-3-Acetylthio-2-methylpropanoyl)-L-prolyl-L-proline tert-butyl ester

The procedure described in the first paragraph of Example 4 was repeated using L-proline tert-butyl ester (0.66 g) in place of L-tyrosine methyl ester. The chloroform solution obtained as in Example 2 was washed successively with 1 N sodium hydroxide, water, 10% citric acid, and water, dried and concentrated under reduced pressure. The residue was chromatographed on silica gel with chloroform to give the title compound, m.p. 99°–103° C.

IR $\nu_{max}^{KBr}$ cm$^{-1}$: 1730, 1680, 1650, 1625.

EXAMPLE 7

1-(D-3-Acetylthio-2-methylpropanoyl)-L-prolyl-L-phenylalanine tert-butyl ester

N-Methylmorpholine (1.03 g) was added to a solution of 1-(D-3-acetylthio-2-methylpropanoyl)-L-proline (2.65 g) in dry tetrahydrofuran (50 ml). The resulting solution was stirred and cooled at −20° to −15° C. Phenyl chloroformate (1.61 g) was added, and after 5 minutes, a solution of L-phenylalanine tert-butyl ester hydrochloride (2.4 g) and N-methylmorpholine (1.03 g) in dry tetrahydrofuran (30 ml) was added. The mixture was stirred at −20° to −15° C. for one hour and then at room temperature overnight. The chloroform solution obtained as in Example 2 was treated as in Example 6. The residue was chromatographed on silica gel with chloroform-methanol (99:1) to give the title compound (4.2 g).

IR $\nu_{max}^{NaCl}$ cm$^{-1}$: 3260, 1715, 1670, 1620.

The following compounds were prepared in substantially the same manner as in Example 7:

1-(D-3-acetylthio-2-methylpropanoyl)-L-prolyl-L-leucine tert-butyl ester, m.p. 113°–115° C. (diethyl ether/n-hexane), IR $\nu_{max}^{KBr}$ cm$^{-1}$: 3230, 1725, 1685, 1660, 1610;

1-(D-3-acetylthio-2-methylpropanoyl)-L-prolylglycine tert-butyl ester, m.p. 119°–120.5° C. (diethyl ether/n-hexane), IR $\nu_{max}^{KBr}$ cm$^{-1}$: 3230, 1715, 1675, 1620;

1-(D-3-acetylthio-2-methylpropanoyl)-L-prolyl-L-alanine tert-butyl ester, m.p. 106°–108° C., IR $\nu_{max}^{KBr}$ cm$^{-1}$: 3240, 1740, 1690, 1675, 1610; and 1-(D-3-acetylthio-2-methylpropanoyl)-L-prolylsarcosine tert-butyl ester, IR $\nu_{max}^{NaCl}$ cm$^{-1}$: 1735, 1685, 1635.

EXAMPLE 8

1-(D-3-Acetylthio-2-methylpropanoyl)-L-prolyl-N$^G$-nitro-L-arginine benzyl ester N-Methylmorpholine (0.39 g) was added to a solution of 1-(D-3-acetylthio-2-methylpropanoyl)-L-proline (1.0 g) in dry tetrahydrofuran (20 ml). The resulting solution was stirred and cooled at −20° to −15° C. Phenyl chloroformate (0.61 g) was added, and after 5 minutes, a solution of N$^G$-nitro-L-arginine benzyl ester di-p-toluenesulfonate (2.54 g) and N-methylmorpholine (0.78 g) in dry tetrahydrofuran (20 ml) was added. The mixture was stirred at −20° to −15° C. for one hour and then at room temperature overnight. The chloroform solution obtained as in Example 2 was washed with 1 N sodium hydroxide and then with water, dried and concentrated under reduced pressure. The residue was chromatographed on silica gel with chloroform-methanol (98:2) to give the title compound (1.2 g).

IR $\nu_{max}^{NaCl}$ cm$^{-1}$: 3250, 1725, 1675, 1605.

EXAMPLE 9

1-(D-3-Mercapto-2-methylpropanoyl)-L-prolyl-L-phenylalanine tert-butyl ester 1-(D-3-Acetylthio-2-methylpropanoyl)-L-prolyl-L-phenylalanine tert-butyl ester (3.2 g) was dissolved under nitrogen in 30% ethanol (50 ml) and the pH of the solution was maintained at 13 for 1.5 hours using 5 N sodium hydroxide.

The reaction mixture was acidified with 10% citric acid and the precipitate was extracted with chloroform. Evaporation of the dried extract under reduced pressure gave the title compound (2.5 g).

IR $\nu_{max}^{NaCl}$ cm$^{-1}$: 3250, 1720, 1660, 1615.

1-(D-3-Mercapto-2-methylpropanoyl)-L-prolyl-L-proline tert-butyl ester was prepared in substantially the same manner as in Example 9, m.p. 79°–84° C. IR $\nu_{max}^{KBr}$ cm$^{-1}$: 2550, 1730, 1640.

EXAMPLE 10

1-(D-3-Mercapto-2-methylpropanoyl)-L-prolyl-L-tyrosine tert-butyl ester 1-(D-3-Acetylthio-2-methylpropanoyl)-L-prolyl-L-tyrosine tert-butyl ester (2.0 g) was suspended under nitrogen in water (40 ml) and the pH of the suspension was maintained at 13 for 1.5 hours using 5 N sodium hydroxide. During this time, the starting material dissolved gradually and a clear solution was obtained after 30 minutes. The reaction mixture was treated as in the second paragraph of Example 9 to give the title compound (1.5 g). IR $\nu_{max}^{NaCl}$ cm$^{-1}$: 3240, 1715, 1645, 1605.

EXAMPLE 11

1-(D-3-Benzoylthio-2-methylpropanoyl)-L-prolyl-L-tyrosine tert-butyl ester 1-(D-3-Mercapto-2-methylpropanoyl)-L-prolyl-L-tyrosine tert-butyl ester (0.70 g) was dissolved under nitrogen in dichloromethane (30 ml), and N-methylmorpholine (162 mg) was added. The resulting solution was cooled in an ice bath, and benzoyl chloride (226 mg) was added dropwise with stirring. After 50 minutes' stirring at room temperature, the reaction mixture was washed successively with 5% sodium bicarbonate, water, 10% citric acid, and water, and dried and concentrated under reduced pressure. The residue was chromatographed on silica gel with chloroform-methanol (99:1) to give the title compound.

IR $\nu_{max}^{NaCl}$ cm$^{-1}$: 3230, 1715, 1650, 1605.

EXAMPLE 12

1-(D-3-Propanoylthio-2-methylpropanoyl)-L-prolyl-L-phenylalanine tert-butyl ester 1-(D-3-Mercapto-2-methylpropanoyl)-L-prolyl-L-phenylalanine tert-butyl ester (1.50 g) was dissolved in dichloromethane (30 ml) under nitrogen and the solution was cooled in an ice bath. N-Methylmorpholine (0.77 g) and then, with stirring, propionyl chloride (0.70 g) were added. After one hour stirring at room temperature, the reaction mixture was washed successively with 1 N sodium hydroxide, water, 10% citric acid, and water, dried and concentrated under reduced pressure. The residue was chromatographed on silica gel with chloroform to give the title compound (1.2 g), m.p. 85°–86° C. (diethyl ether/n-hexane).

IR $\nu_{max}^{KBr}$ cm$^{-1}$: 3280, 1720, 1675, 1635.

The following compounds were prepared in substantially the same manner as in Example 12:

1-(D-3-propanoylthio-2-methylpropanoyl)-L-prolyl-L-proline tert-butyl ester, m.p. 96°–98° C., IR $\nu_{max}^{KBr}$ cm$^{-1}$: 1730, 1685, 1655, 1625;

1-(D-3-butanoylthio-2-methylpropanoyl)-L-prolyl-L-phenylalanine tert-butyl ester, IR $\nu_{max}^{NaCl}$ cm$^{-1}$: 1725, 1680, 1620;

1-[D-3-(2-methylpropanoyl)thio-2-methylpropanoyl]-L-prolyl-L-phenylalanine tert-butyl ester, m.p. 67°–69° C., IR $\nu_{max}^{KBr}$ cm$^{-1}$: 1730, 1680, 1640;

1-[D-3-(2,2-dimethylpropanoyl)thio-2-methylpropanoyl]-L-prolyl-L-phenylalanine tert-butyl ester, m.p. 45°–48° C., IR $\nu_{max}^{KBr}$ cm$^{-1}$: 1730, 1675, 1640;

1-(D-3-benzoylthio-2-methylpropanoyl)-L-prolyl-L-proline tert-butyl ester, IR $\nu_{max}^{NaCl}$ cm$^{-1}$: 1730, 1655; and 1-(D-3-benzoylthio-2-methylpropanoyl)-L-prolyl-L-phenylalanine tert-butyl ester, IR $\nu_{max}^{NaCl}$ cm$^{-1}$: 1730, 1660.

EXAMPLE 13

1-(D-3-Ethyldithio-2-methylpropanoyl)-L-prolyl-L-phenylalanine tert-butyl ester

Diethyl disulfide (214 mg) was dissolved in glacial acetic acid (1 ml), and 30% hydrogen peroxide (196 mg) was added. The solution was allowed to stand overnight, diluted with water (10 ml) and adjusted under cooling to pH 6 with sodium bicarbonate. Because the solution became slightly turbid during this time, ethanol was added to make it clear. To the solution was added an ethanolic solution of 1-(D-3-mercapto-2-methylpropanoyl)-L-prolyl-L-phenylalanine tert-butyl ester (0.70 g). The resulting mixture was allowed to stand at room temperature for 30 minutes, diluted with water, and extracted with dichloromethane. The organic layer was dried over sodium sulfate and concentrated under reduced pressure. The residue was chromatographed on silica gel with chloroform to give the title compound (0.40 g), m.p. 66°–68° C.

IR $\nu_{max}^{KBr}$ cm$^{-1}$: 3280, 1720, 1630.

EXAMPLE 14

1-(D-3-Propyldithio-2-methylpropanoyl)-L-prolyl-L-tyrosine tert-butyl ester

A solution of sodium thiosulfate (41.4 g) in water (63 ml) was added to a solution of n-propyl bromide (20.5 g) in ethanol (42 ml). The mixture was refluxed with stirring for 2 hours and concentrated to dryness under reduced pressure. The residue was washed with diethyl ether and dried to give a white powder. This white powder (0.50 g) was added to a solution of 1-(D-3-mercapto-2-methylpropanoyl)-L-prolyl-L-tyrosine tert-butyl ester (0.77 g) in 50% ethanol (20 ml) containing sodium hydroxide (0.15 g). The resulting mixture was stirred at room temperature for 30 minutes, acidified with 10% citric acid, and extracted with chloroform. The organic layer was dried and concentrated to dryness under reduced pressure. The residue was chromatographed on silica gel with chloroform-methanol (97:3) to give the title compound.

IR $\nu_{max}^{NaCl}$ cm$^{-1}$: 3240, 1720, 1650, 1610.

EXAMPLE 15

1-(D-3-Ethoxycarbonylthio-2-methylpropanoyl)-L-prolyl-L-phenylalanine tert-butyl ester 1-(D-3-Mercapto-2-methylpropanoyl)-L-prolyl-L-phenylalanine tert-butyl ester (1.1 g) was dissolved under nitrogen in dichloromethane (40 ml) and the solution was cooled in an ice bath. N-Methylmorpholine (0.26 g) and then, ethyl chloroformate (0.27 g) were added. After one hour stirring in the ice bath, the reaction mixture was washed with water, dried and concentrated under reduced pressure. The residue was chromatographed on silica gel with chloroform to give the title compound (0.84 g).

IR $\nu_{max}^{NaCl}$ cm$^{-1}$: 3250, 1720, 1690, 1670(sh), 1620.

EXAMPLE 16

1-(D-3-Diethylcarbamoylthio-2-methylpropanoyl)-L-prolyl-L-phenylalanine tert-butyl ester 1-(D-3-Mercapto-2-methylpropanoyl)-L-prolyl-L-phenylalanine tert-butyl ester (0.85 g) was dissolved in pyridine (20 ml) under nitrogen and diethylcarbamoyl chloride (0.87 g) was added. The mixture was stirred at room temperature overnight and then concentrated under reduced pressure. The residue was dissolved in dichloromethane. The solution was washed with 10% citric acid and then with water, dried and concentrated under reduced pressure. The residue was chromatographed on silica gel with chloroform to give the title compound.

IR $\nu_{max}^{NaCl}$ cm$^{-1}$: 1730, 1640.

The following compounds were prepared by repeating the procedure of Example 16 except that ethyl isocyanate or phenyl isothiocyanate was used in place of diethylcarbamoyl chloride:

1-(D-3-ethylcarbamoylthio-2-methylpropanoyl)-L-prolyl-L-phenylalanine tert-butyl ester, IR $\nu_{max}^{NaCl}$ cm$^{-1}$: 1730, 1650, 1625; and 1-(D-3-phenylthiocarbamoylthio-2-methylpropanoyl)-L-prolyl-L-phenylalanine tert-butyl ester, IR $\nu_{max}^{NaCl}$ cm$^{-1}$: 1725, 1655, 1615.

EXAMPLE 17

1-(D-3-Acetylthio-2-methylpropanoyl)-L-prolyl-L-phenylalanine 1-(D-3-Acetylthio-2-methylpropanoyl)-L-prolyl-L-phenylalanine tert-butyl ester (2.5 g) was dissolved in a mixture of anisole (18 ml) and trifluoroacetic acid (37 ml). The solution was allowed to stand at room temperature for one hour and then concentrated to dryness under reduced pressure. The residue was crystallized from diethyl ether. Crystals collected were recrystallized from ethanol/n-hexane to give the title compound (1.8 g), m.p. 155°–156° C.

$[\alpha]_D^{25} = -81.3°$ (c=1.02, ethanol)

IR $\nu_{max}^{KBr}$ cm$^{-1}$: 3240, 1740, 1685, 1645, 1620.

EXAMPLE 18

1-(D-3-Acetylthio-2-methylpropanoyl)-L-prolyl-L-leucine 1-(D-3-Acetylthio-2-methylpropanoyl)-L-prolyl-L-leucine tert-butyl ester (2.0 g) was dissolved in a mixture of anisole (18 ml) and trifluoroacetic acid (37 ml). The solution was allowed to stand at room temperature for one hour and then concentrated to dryness under reduced pressure.

The residue was chromatographed on silica gel with chloroform-methanol (95:5). Fractions containing the title compound were pooled and concentrated under reduced pressure. The residue was crystallized from diethyl ether/n-hexane to give the title compound (1.1 g), m.p. 59°–62° C. IR $\nu_{max}^{KBr}$ cm$^{-1}$: 1680, 1640, 1610(sh).

1-(D-3-Acetylthio-2-methylpropanoyl)-L-prolyl-L-proline was prepared in substantially the same manner as in Example 18, m.p. 164°–169° C.

IR $\nu_{max}^{KBr}$ cm$^{-1}$: 1720, 1685, 1650, 1600.

EXAMPLE 19

1-(D-3-Acetylthio-2-methylpropanoyl)-L-prolylglycine

The procedure described in the first paragraph of Example 18 was repeated using 1-(D-3-acetylthio-2-methylpropanoyl)-L-prolylglycine tert-butyl ester (3.5 g) in place of 1-(D-3-acetylthio-2-methylpropanoyl)-L-prolyl-L-leucine tert-butyl ester. The resulting residue was chromatographed on silica gel with chloroform-methanol (98:2). Fractions containing the title compound were pooled and concentrated under reduced pressure. The residue was recrystallized from dichloromethane/diethyl ether/n-hexane to give the title compound (2.15 g), m.p. 132°–133° C.

IR $\nu_{max}^{KBr}$ cm$^{-1}$: 3240, 1710, 1680, 1670(sh), 1590.

EXAMPLE 20

1-(D-3-Acetylthio-2-methylpropanoyl)-L-prolyl-L-tyrosine

The procedure described in the first paragraph of Example 18 was repeated using 1-(D-3-acetylthio-2-methylpropanoyl)-L-prolyl-L-tyrosine tert-butyl ester (2.0 g) in place of 1-(D-3-acetylthio-2-methylpropanoyl)-L-propyl-L-leucine tert-butyl ester. The resulting residue was chromatographed on silica gel with chloroform-methanol (98:2) to give the title compound (1.4 g).

IR $\nu_{max}^{NaCl}$ cm$^{-1}$: 3250, 1715, 1670(sh), 1650, 1600.

The following compounds were prepared in substantially the same manner as in Example 20:

1-(D-3-ethoxycarbonylthio-2-methylpropanoyl)-L-prolyl-L-phenylalanine, IR $\nu_{max}^{NaCl}$ cm$^{-1}$: 3240, 1690, 1620;

1-(D-3-ethyldithio-2-methylpropanoyl)-L-prolyl-L-phenylalanine, IR $\nu_{max}^{NaCl}$ cm$^{-1}$: 3250, 1720, 1620;

1-(D-3-benzoylthio-2-methylpropanoyl)-L-prolyl-L-phenylalanine, IR $\nu_{max}^{NaCl}$ cm$^{-1}$: 1730, 1655;

1-(D-3-butanoylthio-2-methylpropanoyl)-L-prolyl-L-phenylalanine, IR $\nu_{max}^{NaCl}$ cm$^{-1}$: 1730, 1680, 1620;

1-[D-3-(2-methylpropanoyl)thio-2-methylpropanoyl]-L-prolyl-L-phenylalanine, IR $\nu_{max}^{NaCl}$ cm$^{-1}$: 1730, 1680, 1620;

1-[D-3-(2,2-dimethylpropanoyl)thio-2-methylpropanoyl]-L-prolyl-L-phenylalanine, IR $\nu_{max}^{NaCl}$ cm$^{-1}$: 1730, 1675;

1-(D-3-diethylcarbamoylthio-2-methylpropanoyl)-L-prolyl-L-phenylalanine, IR $\nu_{max}^{NaCl}$ cm$^{-1}$: 1730, 1640;

1-(D-3-ethylcarbamoylthio-2-methylpropanoyl)-L-prolyl-L-phenylalanine, IR $\nu_{max}^{NaCl}$ cm$^{-1}$: 1730, 1640;

1-(D-3-acetylthio-2-methylpropanoyl)-L-prolyl-L-alanine, IR $\nu_{max}^{NaCl}$ cm$^{-1}$: 1730, 1685, 1650, 1600;

1-(D-3-acetylthio-2-methylpropanoyl)-L-prolylsarcosine, m.p. 140°–142° C., IR $\nu_{max}^{KBr}$ cm$^{-1}$: 1730, 1690, 1655, 1600;

1-(D-3-propanoylthio-2-methylpropanoyl)-L-prolyl-L-proline, m.p. 145°–150° C., IR $\nu_{max}^{KBr}$ cm$^{-1}$: 1730, 1670, 1640, 1600; and 1-(D-3-benzoylthio-2-methylpropanoyl)-L-prolyl-L-proline, m.p. 147°–148° C., IR $\nu_{max}^{KBr}$ cm$^{-1}$: 1730, 1655, 1600.

EXAMPLE 21

1-(D-3-Propanoylthio-2-methylpropanoyl)-L-prolyl-L-phenylalanine 1-(D-3-Propanoylthio-2-methylpropanoyl)-L-prolyl-L-phenylalanine tert-butyl ester (0.40 g) was dissolved in a mixture of anisole (3 ml) and trifluoroacetic acid (6 ml). The solution was allowed to stand at room temperature for one hour and then concentrated to dryness under reduced pressure. The residue was partitioned between dichloromethane and 4% sodium bicarbonate. The aqueous solution was acidified with 10% citric acid and extracted with dichloromethane. The organic layer was dried and concentrated under reduced pressure. The residue was crystallized from diethyl ether. Crystals collected were recrystallized from diethyl ether to give the title compound (0.20 g), m.p. 107°–114° C. $[\alpha]_D^{20} = -81.1°$ (c=1.00, ethanol) IR $\nu_{max}^{KBr}$ cm$^{-1}$: 3220, 1730, 1670, 1635, 1610.

EXAMPLE 22

1-(D-3-Mercapto-2-methylpropanoyl)-L-prolylglycine 1-(D-3-Acetylthio-2-methylpropanoyl)-L-prolylglycine (1.0 g) was dissolved in water (20 ml) under nitrogen, and the pH of the solution was maintained at 13 for 1.5 hours using 5 N sodium hydroxide. Then the solution was adjusted to pH 2 with concentrated sulfuric acid, saturated with sodium chloride, and extracted with ethyl acetate. The organic layer was dried over sodium sulfate and concentrated under reduced pressure to give the title compound (0.75 g).

The compound thus obtained (0.50 g) was dissolved in water (50 ml), and calcium hydroxide (68 mg) was added. Lyophilization of the solution gave the calcium salt of the title compound.

IR $\nu_{max}^{KBr}$ cm$^{-1}$: 3370, 1600, 1430.

EXAMPLE 23

1-(D-3-Mercapto-2-methylpropanoyl)-L-prolyl-L-phenylalanine 1-(D-3-Acetylthio-2-methylpropanoyl)-L-prolyl-L-phenylalanine (1.0 g) was suspended in water (20 ml) under argon. The pH of the suspension was maintained at 13 for 1.5 hours using 5 N sodium hydroxide. During this time, the suspension became clear to give a solution. The solution thus obtained was adjusted to pH 2 with concentrated sulfuric acid and extracted with dichloromethane. The organic layer was washed with water, dried and concentrated to give the title compound (0.75 g).

The compound thus obtained (0.50 g) was dissolved in 50% ethanol, and calcium hydroxide (48 mg) was added. The solution was concentrated to dryness under reduced pressure. The residue was dissolved in water (50 ml) and the resulting solution was lyophilized to give the calcium salt of the title compound, m.p. 160°–180° C. (decomposition). IR $\nu_{max}^{KBr}$ cm$^{-1}$: 3380, 1600, 1410.

EXAMPLE 24

1,1'-[3,3'-Dithiobis(D-2-methylpropanoyl)]-bis(L-prolyl-L-phenylalanine)

1-(D-3-Mercapto-2-methylpropanoyl)-L-prolyl-L-phenylalanine (0.16 g) was dissolved in water (20 ml) and the solution was adjusted to pH 6.5 with 1 N sodium hydroxide. While the pH of the solution was adjusted to 6.5, ethanolic iodine was added dropwise until there was a persistent yellow color. Excess iodine was decomposed by adding a small piece of sodium thiosulfate.

The reaction mixture was acidified with concentrated hydrochloric acid and extracted with dichloromethane. The organic layer was washed with water, dried and concentrated to dryness under reduced pressure to give the title compound.

IR $\nu_{max}^{NaCl}$ cm$^{-1}$: 3350, 1720, 1610.

EXAMPLE 25

1,1'-[3,3'-Dithiobis(D-2-methylpropanoyl)]-bis(L-prolylglycine)

The procedure described in the first paragraph of Example 24 was repeated using 1-(D-3-mercapto-2-methylpropanoyl)-L-prolylglycine in place of 1-(D-3-mercapto-2-methylpropanoyl)-L-prolyl-L-phenylalanine. The reaction mixture was acidified with concentrated hydrochloric acid, saturated with sodium chloride, and extracted with ethyl acetate. The organic layer was washed with a saturated aqueous sodium chloride, dried over sodium sulfate, and concentrated to dryness under reduced pressure to give the title compound.

IR $\nu_{max}^{NaCl}$ cm$^{-1}$: 3250, 1720, 1600.

EXAMPLE 26

1-(D-3-Acetylthio-2-methylpropanoyl)-L-prolyl-L-phenylalanine

To a stirred solution of L-prolyl-L-phenylalanine tert-butyl ester (1.0 g) [prepared by the method described in Ann. Chem. 680, 132–141 (1964)] in dichloromethane at about $-30°$ C. were added N-methylmorpholine (0.32 g) and then dropwise 3-acetylthio-2-methylpropanoyl chloride (0.57 g). The mixture was stirred at the same temperature for 30 minutes and then at room temperature for one hour. The reaction mixture was washed successively with 4% sodium bicarbonate, water, 10% citric acid, and water, dried over sodium sulfate, and concentrated under reduced pressure. The residue was chromatographed on silica gel with chloroform to give 1-(3-acetylthio-2-methylpropanoyl)-L-prolyl-L-phenylalanine tert-butyl ester.

The compound thus obtained was dissolved in a mixture of anisole (10 ml) and trifluoroacetic acid (20 ml). The solution was allowed to stand at room temperature for one hour and then concentrated to dryness under reduced pressure.

The residue was dissolved in a small amount of ethanol, and a proper amount of n-hexane was added. The precipitated crystals were collected and recrystallized repeatedly from ethanol/n-hexane to give the title compound, m.p. 155°–156° C. $[\alpha]_D^{25} = -81.3°$ (c=1.02, ethanol)

EXAMPLE 27

1-(D-3-Acetylthio-2-methylpropanoyl)-L-prolyl-L-phenylalanine

To a solution of L-prolyl-L-phenylalanine (0.52 g) in 1 N sodium hydroxide (2 ml) cooled in an ice bath, 3-acetylthio-2-methylpropanoyl chloride (0.36 g) and 2 N sodium hydroxide (1 ml) were added with vigorous stirring. After 3 hours' stirring at room temperature, the solution was washed with diethyl ether, acidified, and extracted with ethyl acetate. The organic layer was dried over sodium sulfate and concentrated to dryness under reduced pressure. The residue was treated as in the third paragraph of Example 26 to give the title compound.

EXAMPLE 28

1-(D-3-Propanoylthio-2-methylpropanoyl)-L-prolyl-L-phenylalanine

L-Prolyl-L-phenylalanine tert-butyl ester (0.70 g) was reacted with 3-propanoylthio-2-methylpropanoyl chloride (0.43 g) in the presence of N-methylmorpholine (0.22 g), and the reaction mixture was treated as in the first paragraph of Example 26.

The 1-(3-propanoylthio-2-methylpropanoyl)-L-prolyl-L-phenylalanine tert-butyl ester obtained was dissolved in a mixture of anisole (10 ml) and trifluoroacetic acid (20 ml). The solution was allowed to stand at room temperature for one hour and concentrated to dryness under reduced pressure. The residue was chromatographed on silica gel with chloroform-methanol (98:2) to give 1-(3-propanoylthio-2-methylpropanoyl)-L-prolyl-L-phenylalanine. The diastereomeric mixture thus obtained was dissolved in a proper amount of diethyl ether. The solution was seeded with crystals of the title compound and stored in a refrigerator. The precipitated crystals were collected and recrystallized repeatedly from diethyl ether/petroleum ether to give the title compound, m.p. 107°-114° C. $[\alpha]_D^{20} = -81.1°$ (c=1.00, ethanol)

EXAMPLE 29

1-(D-3-Propanoylthio-2-methylpropanoyl)-L-prolyl-L-phenylalanine

L-Prolyl-L-phenylalanine tert-butyl ester (0.54 g) was added to a solution of 3-propanoylthio-2-methylpropanoic acid (0.30 g) and dicyclohexylcarbodiimide (0.35 g) in dichloromethane (10 ml) cooled in an ice bath. The mixture was stirred in the ice bath for one hour and then at room temperature overnight, followed by concentration under reduced pressure. Ethyl acetate was added to the residue. After cooling, the precipitates were filtered off. The filtrate was washed, dried and concentrated as in Example 26. The residue was chromatographed as in Example 26 to give 1-(3-propanoylthio-2-methylpropanoyl)-L-prolyl-L-phenylalanine tert-butyl ester.

The compound thus obtained was treated as in the second paragraph of Example 28 to give the title compound.

The starting materials used in Examples 28 and 29 were prepared as follows.

REFERENTIAL EXAMPLE 1

3-Propanoylthio-2-methylpropanoic acid

A mixture of thiopropanoic acid (50 g) and methacrylic acid (34.1 g) was heated on a steam bath for 3 hours and allowed to stand at room temperature overnight. The reaction mixture was distilled under reduced pressure to give the title compound, b.p. 135°-138° C. (2 mmHg).

REFERENTIAL EXAMPLE 2

3-Propanoylthio-2-methylpropanoyl chloride

A mixture of 3-propanoylthio-2-methylpropanoic acid (19.7 g) and thionyl chloride (16 g) was stirred at room temperature overnight. The reaction mixture was distilled under reduced pressure to give the title compound, b.p. 135°-137° C. (35 mmHg).

Compound 3 used in the pharmacological test was prepared as follows:

REFERENTIAL EXAMPLE 3

1-(D-3-Acetylthio-2-methylpropanoyl)-L-proline amide 1-(D-3-Acetylthio-2-methylpropanoyl)-L-proline (2.0 g) and N-methylmorpholine (0.78 g) were dissolved in dichloromethane and the solution was cooled at about −30° C. Phenyl chloroformate (1.2 g) was added with stirring and after 5 minutes, ammonia gas was passed through the mixture over a period of 2 minutes. The mixture was stirred at about −30° C. for an additional 15 minutes and then 10% hydrochloric acid was added under cooling. The resulting mixture was stirred thoroughly. The organic layer was separated, washed with 10% hydrochloric acid and then with water, dried and concentrated under reduced pressure. The residue was chromatographed on silica gel with chloroform-methanol (99:1) to give the title compound.

IR $\nu_{max}^{NaCl}$ cm$^{-1}$: 1690, 1630.

EXAMPLE 30

|  | per 1,000 tablets |
|---|---|
| 1-(D-3-Acetylthio-2-methylpropanoyl)-L-prolyl-L-phenylalanine | 25 g |
| Corn starch | 28 g |
| Lactose | 60 g |
| Microcrystalline cellulose | 30 g |
| Hydroxypropylcellulose | 5 g |
| Light anhydrous silicic acid | 1 g |
| Magnesium stearate | 1 g |

The above components were blended, granulated and compressed into 1,000 tablets each weighing 150 mg by a conventional method. The tablets were further coated with hydroxypropyl methylcellulose, talc, titanium dioxide, and sorbitan fatty acid ester in a customary manner. There were obtained 1,000 coated tablets.

EXAMPLE 31

|  | per 1,000 capsules |
|---|---|
| 1-(D-3-Acetylthio-2-methylpropanoyl)-L-prolyl-L-phenylalanine | 100 g |
| Corn starch | 66 g |
| Lactose | 50 g |
| Microcrystalline cellulose | 30 g |
| Light anhydrous silicic acid | 2 g |
| Magnesium stearate | 2 g |

The above components were blended, granulated and filled into 1,000 capsules by a conventional method.

EXAMPLE 32

The same procedures as in Examples 30 and 31 were repeated except that 1-(D-3-propanoylthio-2-methylpropanoyl)-L-prolyl-L-phenylalanine was used in place of 1-(D-3-acetylthio-2-methylpropanoyl)-L-prolyl-L-phenylalanine. Thus tablets and capsules were prepared respectively.

What we claim is:

1. A compound of the formula

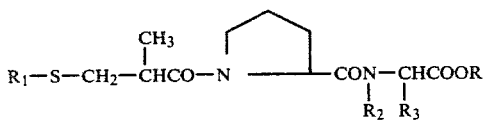

wherein
R represents hydrogen, lower alkyl, phenyl-lower alkyl or substituted phenyl-lower alkyl,
$R_1$ represents $R_4CO—$,
$R_2$ represents hydrogen or lower alkyl,
$R_3$ represents hydrogen, phenyl, lower alkyl, or substituted lower alkyl in which the substituent is hydroxy, phenyl-lower alkoxy, phenyl or hydroxyphenyl,
$R_4$ represents lower alkyl, phenyl, substituted phenyl, phenyl-lower alkyl or substituted phenyl-lower alkyl, the substituent in the substituted phenyl group in the foregoing definition being halogen, lower alkyl or lower alkoxy;
or a pharmaceutically acceptable salt thereof.

2. A compound or a pharmaceutically acceptable salt thereof according to claim 1 wherein $R_3$ represents hydrogen, lower alkyl or substituted lower alkyl in which the substituent is phenyl or hydroxyphenyl.

3. A compound or a pharmaceutically acceptable salt thereof according to claim 1 wherein $R_2$ represents hydrogen.

4. A compound or a pharmaceutically acceptable salt thereof according to claim 3 wherein $R_3$ represents lower alkyl, or substituted lower alkyl in which the substituent is phenyl or hydroxyphenyl.

5. A compound or a pharmaceutically acceptable salt thereof according to claim 3 wherein $R_3$ represents a benzyl or p-hydroxybenzyl group.

6. A compound or a pharmaceutically acceptable salt thereof according to claim 3 wherein $R_3$ represents benzyl.

7. A compound or a pharmaceutically acceptable salt thereof according to claim 1 wherein R represents hydrogen or lower alkyl.

8. A compound or a pharmaceutically acceptable salt thereof according to claim 7 wherein $R_2$ represents hydrogen and $R_3$ represents benzyl.

9. A compound or a pharmaceutically acceptable salt thereof according to claim 1 wherein $R_1$ represents alkanoyl containing 2 to 7 carbon atoms or benzoyl.

10. A compound or a pharmaceutically acceptable salt thereof according to claim 1 wherein R represents hydrogen or lower alkyl, $R_1$ represents lower alkanoyl or benzoyl, $R_2$ represents hydrogen or lower alkyl, and $R_3$ represents hydrogen, lower alkyl, or substituted lower alkyl in which the substituent is phenyl or hydroxyphenyl.

11. A compound or a pharmaceutically acceptable salt thereof according to claim 10 wherein $R_2$ represents hydrogen, and $R_3$ represents lower alkyl, or substituted lower alkyl in which the substituent is phenyl or hydroxyphenyl.

12. A compound or a pharmaceutically acceptable salt thereof according to claim 11 wherein $R_3$ represents a benzyl or p-hydroxybenzyl group.

13. A compound or a pharmaceutically acceptable salt thereof according to claim 11 wherein $R_3$ represents benzyl.

14. A compound or a pharmaceutically acceptable salt thereof according to claim 1 wherein R represents hydrogen or alkyl containing 1 or 2 carbon atoms, $R_1$ represents alkanoyl containing 2 to 7 carbon atoms or benzoyl, $R_2$ represents hydrogen and $R_3$ represents benzyl or p-hydroxybenzyl.

15. A compound of the formula

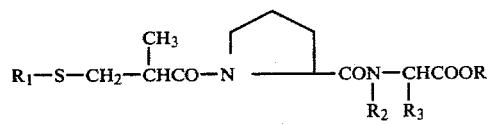

wherein R represents hydrogen or alkyl containing 1 or 2 carbon atoms, $R_1$ represents alkanoyl containing 2 to 7 carbon atoms or benzoyl, $R_2$ represents hydrogen and $R_3$ represents benzyl, or a pharmaceutically acceptable salt thereof.

16. A compound or a pharmaceutically acceptable salt thereof according to claim 15 wherein R and $R_2$ represent hydrogen, $R_1$ represents acetyl, and $R_3$ represents benzyl.

17. A compound or a pharmaceutically acceptable salt thereof according to claim 15 wherein R and $R_2$ represent hydrogen, $R_1$ represents propanoyl, and $R_3$ represents benzyl.

18. A compound or a pharmaceutically acceptable salt thereof according to claim 15 wherein R and $R_2$ represent hydrogen, $R_1$ represents 2,2-dimethylpropanoyl, and $R_3$ represents benzyl.

19. A compound or a pharmaceutically acceptable salt thereof according to claim 15 wherein R and $R_2$ represent hydrogen, $R_1$ represents 2-methylpropanoyl, and $R_3$ represents benzyl.

20. A compound or a pharmaceutically acceptable salt thereof according to claim 15 wherein R and $R_2$ represent hydrogen, $R_1$ represents benzoyl, and $R_3$ represents benzyl.

21. A compound or a pharmaceutically acceptable salt thereof according to any one of claims 1, 10, 11, 12, 13, 14 and 15 wherein the configurations of the proline moiety and $R_3$ are in the L-form.

22. A compound or a pharmaceutically acceptable salt thereof according to claim 21 wherein the configuration of the methyl group at the 2-position of the group

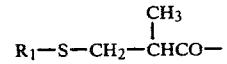

is in the D-form.

23. A compound or a pharmaceutically acceptable salt thereof according to any one of claims 16, 17, 18, 19 and 20 wherein the configurations of the proline moiety and $R_3$ are in the L-form.

24. 1-(D-3-Acetylthio-2-methylpropanoyl)-L-prolyl-L-phenylalanine.

25. 1-(D-3-Propanoylthio-2-methylpropanoyl)-L-prolyl-L-phenylalanine.

26. 1-[D-3-(2,2-Dimethylpropanoyl)thio-2-methylpropanoyl]-L-prolyl-L-phenylalanine.

27. 1-[D-3-(2-Methylpropanoyl)thio-2-methylpropanoyl]-L-prolyl-L-phenylalanine.

28. 1-(D-3-Benzoylthio-2-methylpropanoyl)-L-prolyl-L-phenylalanine.

29. A method of treating hypertension in mammals which comprises administering an antihypertensive effective amount of a compound or a pharmaceutically acceptable salt thereof according to claim 1.

30. A pharmaceutical composition comprising an antihypertensive effective amount of a compound or a pharmaceutically acceptable salt thereof according to claim 1, and a pharmaceutically acceptable carrier.

31. A method of treating hypertension in mammals which comprises administering an antihypertensive effective amount of a compound or a pharmaceutically acceptable salt thereof according to claim 15.

32. A method of treating hypertension in mammals which comprises administering an antihypertensive effective amount of a compound or a pharmaceutically acceptable salt thereof according to claim 16.

33. A method of treating hypertension in mammals which comprises administering an antihypertensive effective amount of a compound or a pharmaceutically acceptable salt thereof according to claim 17.

34. A method of treating hypertension in mammals which comprises administering an antihypertensive effective amount of a compound or a pharmaceutically acceptable salt thereof according to claim 24.

35. A method of treating hypertension in mammals which comprises administering an antihypertensive effective amount of a compound or a pharmaceutically acceptable salt thereof according to claim 25.

36. A pharmaceutical composition comprising an antihypertensive effective amount of a compound or a pharmaceutically acceptable salt thereof according to claim 15, and a pharmaceutically acceptable carrier.

37. A pharmaceutical composition comprising an antihypertensive effective amount of a compound or a pharmaceutically acceptable salt thereof according to claim 16, and a pharmaceutically acceptable carrier.

38. A pharmaceutical composition comprising an antihypertensive effective amount of a compound or a pharmaceutically acceptable salt thereof according to claim 17, and a pharmaceutically acceptable carrier.

39. A pharmaceutical composition comprising an antihypertensive effective amount of a compound or a pharmaceutically acceptable salt thereof according to claim 24, and a pharmaceutically acceptable carrier.

40. A pharmaceutical composition comprising an antihypertensive effective amount of a compound or a pharmaceutically acceptable salt thereof according to claim 25, and a pharmaceutically acceptable carrier.

* * * * *